United States Patent
Anderson et al.

(10) Patent No.: US 7,438,710 B2
(45) Date of Patent: Oct. 21, 2008

(54) DISTAL PROTECTION DEVICE WITH LOCAL DRUG INFUSION BY PHYSICIAN TO MAINTAIN PATENCY

(76) Inventors: Kent D. Anderson, 11205 Virginia Avenue North, Champlin, MN (US) 55316; Jennifer L. Pavlovic, 5381 St. Croix Trail South, Afton, MN (US) 55001; Sivaprasad Sukavaneshvar, 858 N. Oaktree Ct., #227, Salt Lake City, UT (US) 84116

( * ) Notice: Subject to any disclaimer, the term of this patent is extended or adjusted under 35 U.S.C. 154(b) by 508 days.

(21) Appl. No.: 10/290,392

(22) Filed: Nov. 7, 2002

(65) Prior Publication Data
US 2003/0088211 A1    May 8, 2003

Related U.S. Application Data

(60) Provisional application No. 60/337,936, filed on Nov. 7, 2001.

(51) Int. Cl.
*A61M 31/00* (2006.01)

(52) U.S. Cl. .................................................. 604/508

(58) Field of Classification Search .............. 606/200, 606/192–194, 585; 604/523, 264, 35, 96.01, 604/101.03, 101.01, 101.04, 95.01–95.05, 604/97.01, 97.02, 102.02, 164.13, 266–268, 604/508–510, 528, 103.01
See application file for complete search history.

(56) References Cited

U.S. PATENT DOCUMENTS

| | | | | |
|---|---|---|---|---|
| 5,709,874 A | * | 1/1998 | Hanson et al. | 424/423 |
| 5,776,100 A | | 7/1998 | Forman | |
| 6,013,093 A | | 1/2000 | Nott et al. | |
| 6,022,336 A | * | 2/2000 | Zadno-Azizi et al. | 604/101.05 |
| 6,152,141 A | * | 11/2000 | Stevens et al. | 128/898 |
| 6,168,579 B1 | * | 1/2001 | Tsugita | 604/509 |
| 6,203,561 B1 | | 3/2001 | Ramee et al. | |
| 6,231,589 B1 | | 5/2001 | Wessman et al. | 606/200 |
| 6,402,736 B1 | | 6/2002 | Brown et al. | 604/523 |
| 6,485,500 B1 | * | 11/2002 | Kokish et al. | 606/194 |
| 6,620,148 B1 | * | 9/2003 | Tsugita | 604/509 |
| 6,663,613 B1 | * | 12/2003 | Evans et al. | 604/523 |
| 6,896,691 B2 | * | 5/2005 | Boylan et al. | 606/200 |
| 2002/0188276 A1 | * | 12/2002 | Evans et al. | 604/509 |
| 2003/0139751 A1 | * | 7/2003 | Evans et al. | 606/127 |

FOREIGN PATENT DOCUMENTS

| | | |
|---|---|---|
| WO | WO 01/08743 A1 | 2/2001 |
| WO | WO 03/059205 A2 | 7/2003 |

\* cited by examiner

*Primary Examiner*—Matthew F Desanto
(74) *Attorney, Agent, or Firm*—Popovich, Wiles & O'Connell, P.A.

(57) ABSTRACT

The present invention provides for a local drug delivery mechanism for use with a protection device. An infusing device is used to charge the drug into the catheter lumen toward a distal portion of the lumen having a plurality of drug delivery exit ports. The drug exits the ports into the patient's vascular system and is able to flow toward a filter maintaining the patency of the filter.

11 Claims, 2 Drawing Sheets

DISTAL PROTECTION DEVICE WITH LOCAL DRUG INFUSION BY PHYSICIAN TO MAINTAIN PATENCY

CROSS-REFERENCE TO RELATED APPLICATIONS

This is a regular application filed under 35 U.S.C. §111(a) claiming priority, under 35 U.S.C. § 119(e) (1), of provisional application Ser. No. 60/337,936, previously filed Nov. 7, 2001 under 35 U.S.C. § 111(b).

BACKGROUND OF THE INVENTION

1. Field of the Invention

The present invention generally relates to medical devices for filtering or removing matter from within a vascular system and the delivery of drugs to maintain continued filter patency. More specifically, the present invention relates to protective measures employing a drug delivery system for facilitating patency of the medical device. This device also relates to any other interventional applications where patency must be maintained. This includes such apparatus as stents, grafts, vessel liners and flow diverters.

2. Description of Related Art

Protective devices, generally, include an expandable filter attached to a hostwire. Protective devices are often employed in interventional cardiology/radiology applications to allow the flow of fluid, such as blood, while preventing the passage of particulate matter, such as emboli. Protective devices are often referred to as distal protection devices where the term 'distal' refers to the positioning of the device distal to a lesion or treatment site, with respect to fluid flow in a vessel. The filter portion of existing protection devices may include such items as braided meshes, woven fabrics, perforated films, a plurality of crossing wires, electrospun polymers and any other configuration suitable for filtering.

The performance of the protective device requires that the filter maintain patency. Patency is defined as the ability of the filter to allow the passage of fluid. Patency may refer to the patency of a filter at a specific point in time and/or the amount of time that a filter is able to maintain fluid flow. When used in a vascular system, the patency of the filter decreases over a period of time. As the pore size of the filter decreases, the patency will decrease relative to the patency for a greater pore size. For example, in some filters, when the maximum pore size is 100 um there may be pores ranging in size from 20 um or less. Such a fine pore size may cause a filter to become occluded by debris. Pores below a crucial pore size may also become occluded by formation of an impermeable fibrous sheet that may close off flow through the pore.

The current art utilizes three different mechanisms for facilitating patency.

The first mechanism used in the art involves the use of coatings on the filter to prevent blood clotting. Such coatings include anti-coagulants or anti-thrombogenic or anti-platelet or other such drugs, such as Heparin. Even with such coatings, the patency of the filter is limited because the drug coating is eventually overcome by clotting forces in the blood. Thus, this mechanism results in the patency beginning to decrease as soon as the coating contacts the clotting agents of the blood, and it is only a matter of time before filter patency is reduced or eliminated by the clotting agents.

Two other mechanisms used to provide for increased filter patency include dipping the filter in an anti-coagulant such as a Heparin solution, or a systemic use of drugs such as a IIb/IIIa inhibitor. Even with dipping in Heparin, the patency of the filter will deteriorate over a relatively short period of time. Problems with systemic use of drugs may manifest themselves as excessive patient bleeding.

SUMMARY OF THE INVENTION

The present invention is drug delivery system for facilitating the patency of a filter positioned within a patient's vascular system. An embodiment of the present invention includes a tubular member having a side wall defining an inner lumen. A distal portion of the lumen has a plurality of exit ports extending through the side wall. The proximal end of the tubular member is able to mate with a drug loaded syringe. The drug is charged into the lumen to the distal portion of the tubular member where the drug is able to exit through the exit ports.

The tubular member may be secured to a hostwire, proximal to the expandable filter of the protection device. The expandable filter is secured to the hostwire.

In use, the protection device is deployed in a patient's vascular system. The drug is delivered into the tubular member and is infused into the patient's vascular system through the exit ports of the tubular member. The drug enters the patient's blood within the patient's blood vessel and flows toward the filter for local delivery of the drug for maintaining filter patency. Interventional devices such as PTCA catheters or stents are advanced over the tubular member to a region of interest. The region of interest is treated and emboli released are captured from the bloodstream by the filter. The treatment device, filter, and emboli are removed from the region of interest.

Local drug infusion helps to maintain patency of the filter while blood is flowing through the filter. Local drug infusion provides the anti-coagulation effects of the drug in a local concentration where needed, to maintain filter patency while minimizing the possible side effects (i.e. excessive bleeding) that the drug could cause if used systemically. Generally, the drug is delivered upstream of the filter, proximal to the filter, and allowed to flow distally, through the filter with the blood.

DETAILED DESCRIPTION OF THE INVENTION

Figure 1:
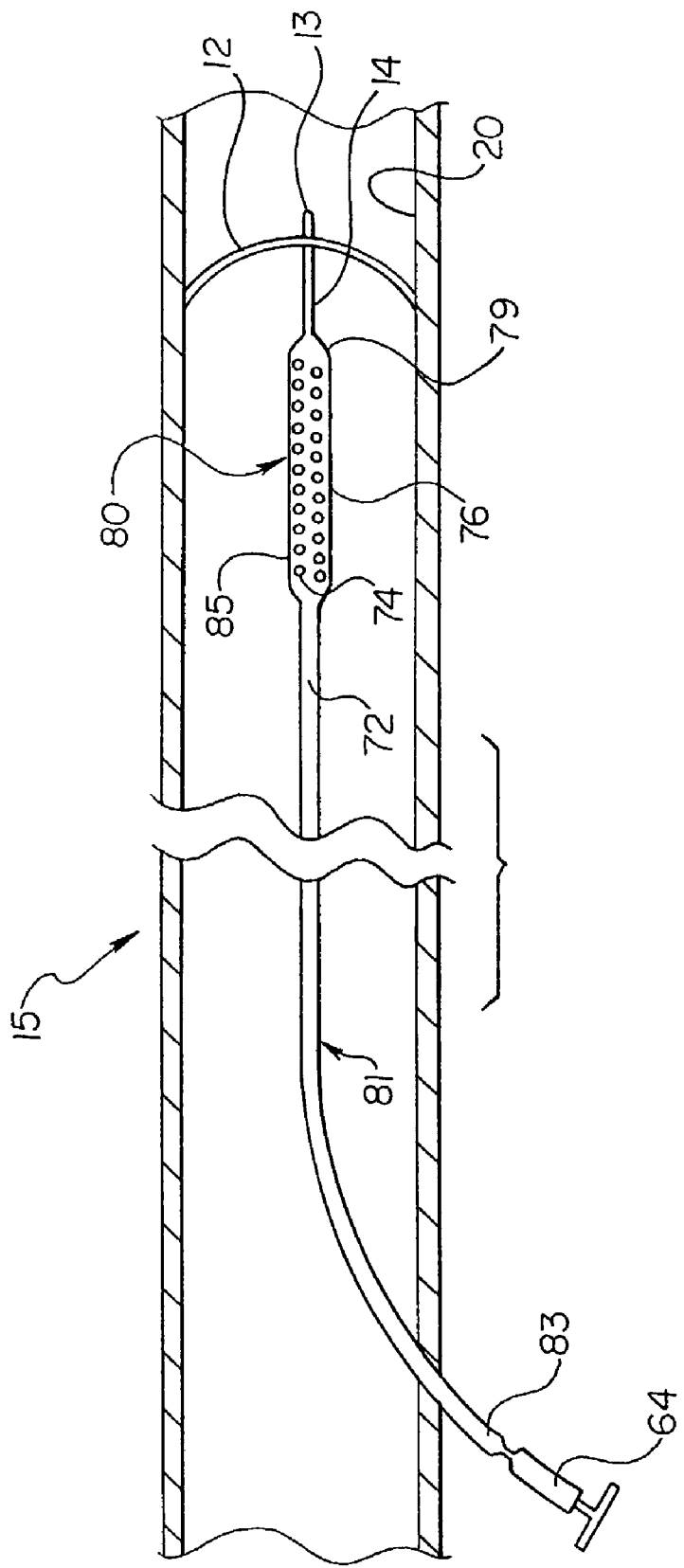
FIG. 1 is a side view of the present invention, some portions broken away.

The present invention, illustrated in FIG. 1, is a distal protection apparatus 15 having the capability of local delivery of a drug to an expandable filter 12 positioned in a lumen 20 in a patient's body. A tubular member 81 extends from a proximal end 83 to a distal end 79. The tubular member 81 has a wall 76 defining a lumen 72 through member 81. The distal end 79 of the tubular member 81 comprises a portion 80 having a cavity defined therewithin and has a plurality of exit ports 74 in the wall 76, thus forming a drug delivery portion or head 80 of the distal protection apparatus 15.

Distal protection apparatus 15 is illustrated having a hostwire 14 to which is mounted an expandable filter 12 at a distal end 13 of the hostwire 14. The distal end of the tubular member 81 is attached to the proximal end of hostwire 14.

The present invention is intended for use in a patient's vascular system. In operation, an infusing device, such as a syringe 64, is filled with a drug for facilitating filter patency within a blood vessel. The syringe 64 is mated to the proximal end 83 of the distal protection apparatus 15, and the drug is charged into the lumen 72. Optionally a removable hub can be provided at the proximal end 83 of the apparatus 15. The drug flows toward the distal end 79 and exits the lumen 72 through the exit ports 74. As the drug is released from the drug delivery portion 80 of the distal protection apparatus 15, the drug is locally delivered into the blood of a patient's vascular system and is carried toward the filter 12 for maintaining patency of the filter 12.

Local drug infusion helps to maintain patency of the filter 12 to ensure blood is flowing through the filter. Local drug infusion provides the anti-coagulation effects of the drug in a local concentration, where needed, to maintain filter patency while minimizing possible side effects (i.e., excessive bleeding) that the drug could cause if used systemically.

The infusing device 64 in FIG. 1 is shown as a syringe. The drug is loaded in the infusing device 64 for introducing the drug into the lumen 72. The drug delivery portion 80 has a first, proximal end 85 at which the dispensing portion of the tubular structure 81 mates with delivery portion 80 for dispensing the drug from lumen 72 which is defined by elongate tubular structure 81. It will be understood that portion 80 can be enlarged, constant, or reduced in diameter as compared to dispensing portion of tubular structure 81.

As illustrated, the delivery ports 74 may be a plurality of apertures spaced about the wall 76 of the drug delivery portion 80. The apertures 74 form channels from the interior of portion 80 to the exterior of the wall 76. This allows the drug to be delivered from within the lumen 72 to the exterior of portion 80. As the drug is released, it is delivered to the area of filter 12 of the distal protection apparatus 15. The drug is then able to facilitate continued patency of filter 12.

In operation, a physician fills the syringe 64 with the appropriate drug and mates the syringe to the proximal end 83 of the distal protection apparatus. The drug is then dispensed from the syringe 64 into the lumen 72.

An intended use for the present invention is in a patient's body such as during a medical procedure. For example, the device can be used in a patient's vascular system such as a blood vessel. The filter 12 can be deployed within the blood vessel so as to filter emboli and particulate matter entrained in the blood of the patient.

The physician may position the distal protection apparatus 15 within the patient's vascular system and deploy the filter 12 such that the periphery of the filter 12 engages the wall of the blood vessel within which the device is deployed. Syringe 64 with a predetermined amount and type of drug may be mated to the proximal end 83 of the tubular structure 81 so as to allow charging of the drug into the apparatus 15. The drug is dispensed from the syringe 64 into the lumen 72. Once the drug is introduced into the lumen 72, the drug is infused through the delivery ports 74 in wall 76 of the lumen 72. The drug is then delivered into the bloodstream and is able to flow to the filter 12. The local release of the drug near the filter 12 allows for increased filter 12 patency even with a filter 12 having a smaller pore size.

Figure 2:
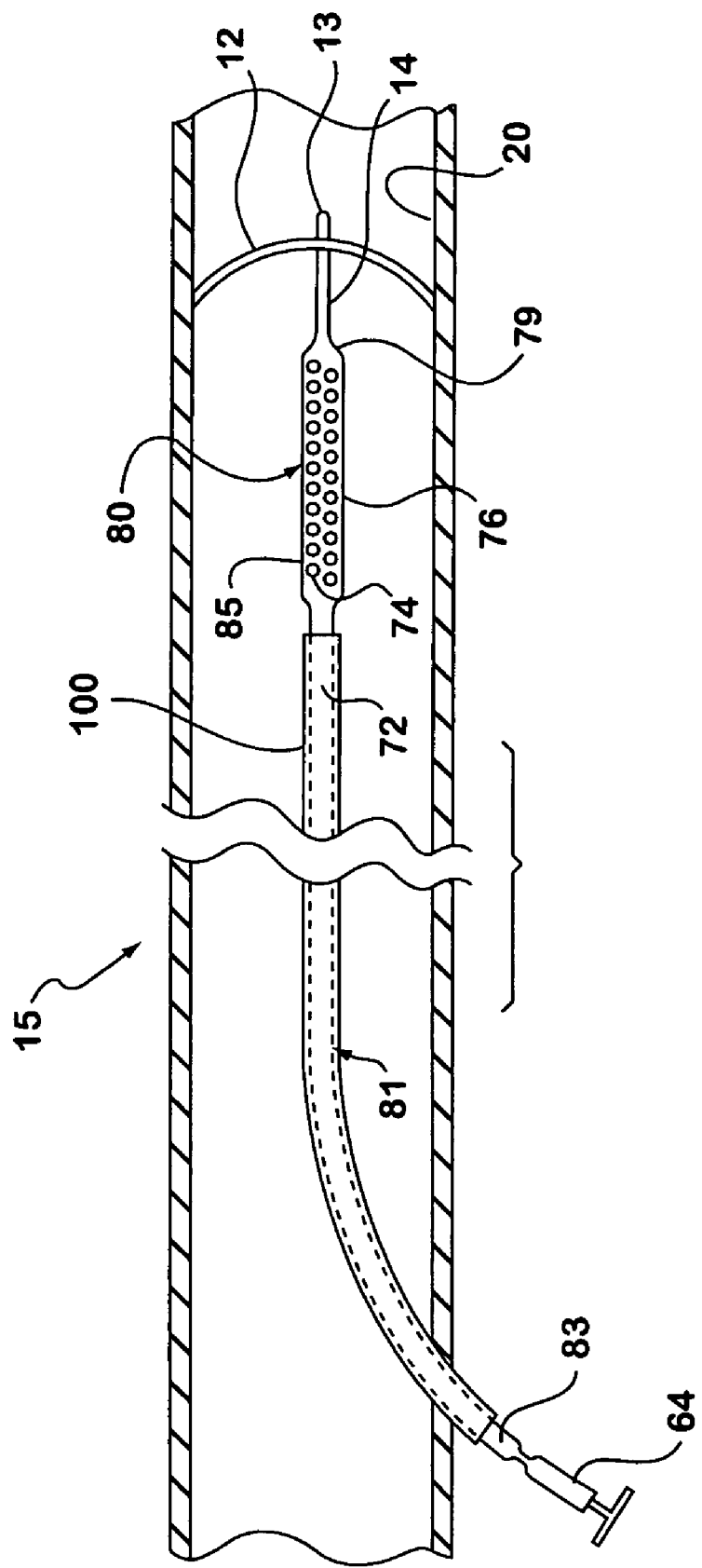
FIG. 2 is a side view of the present invention, some portions broken away.

A treatment device 100 is introduced over the tubular member 81 and a region of interest is treated. See FIG. 2. For example, a PTCA catheter may be used to dilate a stenosis, a stent may be delivered and expanded within a lesion, or a thrombectomy device may be advanced to remove thrombus. Optionally, a drug may be infused periodically during or before the procedure to help maintain patency.

Typically the filter would be recovered by withdrawing the apparatus into a catheter, such as a delivery catheter or a balloon catheter, following the procedure.

The drug delivery may also prevent or remove thrombi or buildup within the blood vessel that is captured in the filter 12 or collected near filter 12. Such build-up could otherwise remain within the blood vessel after the filter 12 has been retracted or removed from the blood vessel.

Other structure for delivering the drug include a pump powered by induction, a screw drive and an elastomer drive, preferably used in conjunction with the syringe 64.

The delivery ports 74 may be spaced in a variety of arrangements in the wall 76. For example, the delivery ports 74 may be spaced circumferentially at various positions along the axial dimension of the wall 76, patterned along the length of the wall 76, spaced so as to wind about the length of the wall 76, and any combination or other means of spacing, random or ordered, so as to provide delivery of a drug from the lumen 72.

The spacing and sizing of the apertures 74 may be configured to control the rate of infusion of the drug into the blood vessel. The apertures 74 may have a predetermined size and spacing that allows for a slower or faster relative rate of infusion. Controlling the rate of infusion may lessen the shear stresses on blood flowing toward the filter 12. A lesser shear stress is preferable over a high pressure drug delivery that may create an accelerated flow pattern which could be detrimental to flow dynamics surrounding the filter 12.

The delivery rate and concentration of the drug may also play a role in the efficacy of operation. For example, a lower concentration drug solution can be delivered at a faster rate, or a higher concentration drug solution can be delivered at a slower rate.

After the drug is delivered through the delivery ports 74, it is infused within the fluid flowing external to portion 80. For example, if the tubular member 81 is positioned within a bloodstream, the drug will become infused within the blood stream. As the blood stream is flowing toward the filter 12, the filter 12 being downstream, the drug will likewise be delivered to the filter 12 from an upstream location. Infusing the drug upstream from the filter 12 and allowing it to flow to the filter 12 may also effect delivery of the drug to local stasis areas in the vicinity of the filter 12 where it can minimize and/or prevent clotting and coagulation. This may result in flushing of loose, partially adherent emboli that may otherwise become dislodged during or after filter 12 removal.

The shape and size of the filter 12 are not critical to the efficacy of the present invention. The filter 12 may assume a variety of configurations such as a basket, a windsock, a flat shape and any number of elongated shapes. The filter 12 may have a cover. The filter 12 merely must perform the function of preventing the passage of particulate material of a predetermined size. The present invention addresses the delivery of a drug to a filter 12 to facilitate filter patency and contemplates the drug delivery system disclosed herein as functioning with a variety of filter sizes, shapes and configurations.

The filter 12 may be attached to the distal portion of a hostwire 14, as shown. The hostwire 14 may extend through the lumen 72 containing the drug. Alternatively, the hostwire 14 may have a drug delivery portion 80 for containing and delivering the drug therefrom.

Possible drugs to be used in the present invention include IIb/IIIa inhibitors and any other such anti-platelet agent, anti-coagulant, lytic, and thrombus-stabilizing agent or any other such drug, such as Heparin, Integrilin or Aggrastat, or drug combinations for preventing occlusions to the filter during a medical procedure. Such drugs help to maintain filter patency even with reduced filter pore size without negative effects of systemic drug administration such as excessive bleeding.

The infusion capabilities of the present invention may also provide the physician or operator the ability to take a diagnostic blood sample at the filter 12 to assess platelet activity and thereby assist in the determination of the appropriate drug or drug combination to administer. Apparatus for determining coagulation activity of blood and the response of a patient's blood to a platelet inhibitor are known to those in the art. A physician could obtain samples by pulling a vacuum on the drug delivery lumen 72 such as by pulling back on an empty syringe.

The present invention may include a relatively stiff yet flexible tube such as a hypotube with a plurality of weep holes 74. The tube could be metallic (e.g. Nitinol or stainless steel), liquid crystal composite, carbon fiber and composites of same, other composites, ceramic, or other material known in the art. Alternatively, the entire tubular member 81, including the drug delivery portion, could be of a flexible material with a plurality of weep holes 74 at a distal end 79 thereof.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. A method for maintaining patency of a filter comprising:
   (i) providing a medical device comprising:
      a filter which permits passage of a fluid therethrough;
      a patency maintenance drug introduction head, positionable in a vessel in an animal body proximate and upflow relative to the filter, for dispensing a patency maintenance drug;
      an elongate member having a lumen therethrough, a distal end in fluid communication with a cavity in the drug introduction head and a proximal end remote from the drug introduction head;
      a reservoir at the proximal end of the elongate member and in fluid communication with the lumen; and
      a charger, associated with the reservoir, for volitionally urging patency maintenance drug in the reservoir into and through the lumen, into the cavity, and out of the drug introduction head;
   (ii) placing the filter and the drug introduction head in a stationary position in the vessel in an animal body through which fluid flow occurs, the filter and the drug introduction head allowing fluid flow through the vessel;
   (iii) dispensing a patency maintenance drug through the drug introduction head, wherein the patency maintenance drug maintains the patency of the filter; and
   (iv) while the filter and the drug introduction head remain in the stationary position, advancing a treatment device distally to a region of interest that is proximal and upflow relative to the filter and treating the region of interest with the treatment device,
   wherein the treatment device is advanced over the elongate member to the region of interest.

2. The method of claim 1, wherein the drug introduction head includes a wall which defines the cavity therewithin, and wherein the wall has a plurality of exit ports passing therethrough.

3. The method of claim 2, wherein the reservoir and the charger comprise a syringe mated to the elongate member at the proximal end thereof.

4. The method of claim 3, wherein the drug introduction head and the elongate member are unitarily formed.

5. The method of claim 4, wherein the drug introduction head comprises an enlarged portion of the elongate member.

6. The method of claim 1, wherein the filter is expandable about a hostwire.

7. The method of claim 1, wherein the filter has a hostwire extending within said elongate member.

8. The method of claim 1, wherein the drug introduction head is positioned downflow relative to the region of interest.

9. The method of claim 1, wherein the treatment device is a PTCA catheter.

10. The method of claim 1, wherein the treatment device is a stent.

11. The method of claim 1, wherein the treatment device is a thrombectomy device.

* * * * *